(12) United States Patent
Reck et al.

(10) Patent No.: US 9,939,115 B2
(45) Date of Patent: Apr. 10, 2018

(54) HOSE COMPRISING AN INTEGRATED SYSTEM FOR DETECTING DAMAGE

(71) Applicant: Eddelbüttel & Schneider GmbH, Hamburg (DE)

(72) Inventors: Siegfried Reck, Nienburg (DE); Guido Wetzel, Neuburg (DE)

(73) Assignee: Eddelbüttel & Schneider GmbH, Hamburg (DE)

( * ) Notice: Subject to any disclaimer, the term of this patent is extended or adjusted under 35 U.S.C. 154(b) by 0 days.

(21) Appl. No.: 15/318,575

(22) PCT Filed: Apr. 28, 2015

(86) PCT No.: PCT/EP2015/059114
§ 371 (c)(1),
(2) Date: Dec. 13, 2016

(87) PCT Pub. No.: WO2015/193012
PCT Pub. Date: Dec. 23, 2015

(65) Prior Publication Data
US 2017/0130905 A1 May 11, 2017

(30) Foreign Application Priority Data

Jun. 19, 2014  (DE) .................. 10 2014 211 798

(51) Int. Cl.
*G01N 27/02* (2006.01)
*F17D 5/06* (2006.01)
*F16L 11/12* (2006.01)
*F16L 57/06* (2006.01)

(52) U.S. Cl.
CPC ............ *F17D 5/06* (2013.01); *F16L 11/12* (2013.01); *F16L 57/06* (2013.01); *G01N 27/02* (2013.01)

(58) Field of Classification Search
CPC ......... F16L 11/12; F16L 57/06; G01N 1/2226
See application file for complete search history.

(56) References Cited

U.S. PATENT DOCUMENTS

| 5,927,342 A * | 7/1999 | Bogut | ................ F16L 11/127 138/103 |
| 2004/0129092 A1 | 7/2004 | Dietzel | |
| 2006/0196252 A1 | 9/2006 | Deckard | |
| 2006/0201566 A1* | 9/2006 | Brink | ................... F16L 33/01 138/109 |

(Continued)

FOREIGN PATENT DOCUMENTS

| DE | 102012112450 A1 | 6/2014 |
| JP | 2007132371 | 5/2007 |

(Continued)

*Primary Examiner* — Jermele M Hollington
*Assistant Examiner* — Alvaro Fortich
(74) *Attorney, Agent, or Firm* — David L. Cate

(57) ABSTRACT

The invention relates to a hose (7) featuring an integrated system for detecting damage and comprising a hose wall (2, 4) in which at least one transponder (8) is embedded. The hose (7) is characterized in that an antenna (12) is also embedded in the hose wall (2, 4) so that an electromagnetic coupling (10) can be established between the antenna (12) and the transponder (8), the magnitude and/or quality of the electromagnetic coupling (10) being a measure of the degree of damage to the hose wall (2, 4).

20 Claims, 4 Drawing Sheets

(56) References Cited

U.S. PATENT DOCUMENTS

2010/0174495 A1 7/2010 Pereira et al.
2013/0314213 A1* 11/2013 Zogg .................. G06K 7/10316
340/10.1

FOREIGN PATENT DOCUMENTS

WO 2011137539 A1 11/2011
WO 2012097241 A1 7/2012

* cited by examiner

HOSE COMPRISING AN INTEGRATED SYSTEM FOR DETECTING DAMAGE

The invention relates to a hose with an integrated system for detecting damage according to the preamble of claim 1.

In order to transport spoil such as e.g. rock, sand and mud from bodies of water, hoses are used which can be up to 3 m in diameter. Such dredging hoses can be made up of segments in order to adapt the length thereof to the particular application and so that only individual segments have to be exchanged in the case of damage.

Damage to the hose wall from the inside frequently occurs in these applications because the spoil to be transported is abrasive. As a result, during operation the inside of the hose wall becomes worn and eroded, i.e. the wall thickness is reduced until finally ruptures occur in the hose wall and therefore spoil material can escape and transportation functions can be lost. In this context, the extent of wear depends to a great extent on the spoil material and the transportation speed, and the wear in the interior of the dredging hose therefore cannot be predicted. However, damage to the dredging hose brings about a stoppage of the conveying process, so that imminent damage needs to be detected in good time.

For this purpose, visual inspections of the inside of the hose wall can be carried out. This is usually done by persons who perform a purely visual inspection of the hose wall from the inside, for which reason the conveying process is interrupted for this purpose and the dredging hose has to be emptied and laid out on the land. This gives rise to a large amount of expenditure and interrupts the conveying process, making this method very time-consuming and costly.

In order to assist the inspection by personnel it is known to introduce colored layers into the hose wall, so that during the inspection the inner side of the hose wall the abrasion per se and the extent of abrasion can be detected visually more easily as a result of the coloring of the exposed hose layers. Although this facilitates the inspection by personnel and increases the prediction possibilities with respect to the extent of abrasion, it does not change anything in terms of the expenditure and the costs of the inspection by personnel.

DE 690 13 336 T2 relates to a wear indicator for material replacement systems, wherein an abrasively acting plastic granulate is transported here. The actual hose is sheathed with colored wear indicators and an outermost translucent safety layer which surrounds said indicators so that a visual inspection of the wear can be carried out from the outside through the safety layer to determine whether the colored wear indicators are still present from the outside or whether they have already been abraded. This system requires accessibility and the possibility of performing a visual inspection from the outside and from all sides of the hose to be monitored during the operation, for which reason it cannot be applied to the dredging hoses described above which are generally used in water over the greater part of their length.

DE 10 2012 112 450.7 proposes introducing a plurality of transponders in one or more cross sections of the hose wall of a dredging hose in such a way that they lie radially one on top of the other at various depths of the hose wall, and detecting their presence from the outside through the hose wall using a reading device. If individual transponders are lost as a result of the abrasion during the operation from the inside, their absence can be detected from the outside by the reading device, and as a result the remaining wall thickness at this location can be determined. However, this method can be applied only if the surroundings of the dredging hose are dry because the connection between the transponders and the reading device is made via high-frequency electromagnetic fields which cannot propagate in water.

In order to monitor a hose for transporting ores and the like in the mining industry, US 2004/0065377 A1 proposes introducing an electrically conductive path into the hose wall and monitoring and evaluating its electrical properties. The intention here is to detect an unacceptably large reduction in the wall thickness of the hose as a result of damage to the electric conductive path. However, this system provides only unreliable information about the abrasion of the inner wall of the hose because punctual damage or damage to a small area of the inner wall can also bring about such a change in the electrical properties of the electric conductive path with the result that this change can be incorrectly interpreted as unacceptable abrasion. Also, in this way the position of the critical abrasion can only be determined very imprecisely on the basis of the changed electrical properties.

For this purpose, DE 699 32 950 T2 also describes a plurality of wear-sensing elements which are each arranged in a sensed layer at different distances from the inside of the hose wall. The wear-sensing elements supply information about the propagation of the wear in the hose to the outside in a line-bound fashion. Owing to its special sensed layers and wear-sensing elements and the cabling for the latter through the hose wall, this system is very complex and therefore expensive.

An object of the present invention is to make available a hose with an integrated system for detecting damage of the type mentioned at the beginning so that the thickness of the hose wall at specific points can be determined during operation as easily as possible and with the best possible precision, from the outside, in particular from the end of the hose or hose segment.

The object is achieved according to the invention by means of a hose with an integrated system for detecting damage, having the features according to claim 1. Advantageous developments are described in the dependent claims.

The present invention therefore relates to a hose with an integrated system for detecting damage, having a hose wall into which at least one transponder is embedded. Such hoses are known e.g. from DE 10 2012 112 450.7. However, there the transponders are eroded out of the hose wall from the inside as a result of the abrasion, their absence is detected and the remaining wall thickness is determined therefrom in discrete gradations.

However, in the case of the hose according to the invention an antenna is also embedded in the hose wall so there can be electromagnetic coupling between the antenna and the transponder, wherein the strength and/or quality of the electromagnetic coupling is a measure of the extent of damage to the hose wall.

To be more precise, the strength and/or the quality of the electromagnetic coupling depends on the mass of the material of the hose wall, in particular on the wear layer, which can be penetrated between the antenna and the transponder by the electromagnetic coupling.

The invention is based here on the concept that the signal strength or the quality (RSSI=Received Signal Strength Indicator (RSSI)) of electromagnetic coupling such as e.g. of a radio link between the transmitter and receiver, here an antenna and a transponder, depends on the medium through which the radio link passes. If this medium changes, the signal strength or quality of the radio link also changes.

In the present case, this means that in a hose this radio link passes through its hose wall and/or through its medium-conducting interior, which is filled with medium during operation. In this context, the hose wall and the empty or filled interior respectively have different (di)electric properties. In addition, when the thickness of the hose wall is reduced by abrasion by the medium to be conveyed, the interior of the hose is increased to the same extent. Therefore, as a result the signal strength or the quality of the radio link which passes through these two areas of the hose wall and the interior of the hose also changes. If this change in the signal strength or the quality of the radio link is detected and evaluated in relation to the previous values or a starting value, e.g. an undamaged hose, detection can be carried out continuously from the outside during the operation of the hose. Specific statements about the extent of wear can also be made for the area of the transponder or the area of the radio link.

The hose is here preferably a flexible, elastic hose which is composed e.g. from an elastomer material such as e.g. rubber or comprises the latter. The hose is preferably designed to convey abrasive materials such as e.g. rock, sand and mud containing fluids such as water. Such hoses are also used as dredging hoses for extracting such materials from bodies of water.

According to one aspect of the present invention, the hose wall has an outer minimum layer and an inner wear layer so that when the wear layer is eroded the thickness of the minimum layer is sufficient to ensure still reliable operation of the hose.

These layers can be composed of different or identical materials. Their difference is rather attributable to the minimum wall thickness which the minimum layer must have for operation of the hose still to be reliably possible. The rest of the inner wall thickness, i.e. the wear layer, can, however, be subjected to abrasion without the operation of the hose having to be ended as a result.

It is advantageous here that in fact unavoidable abrasion which occurs as a result of operation can be tolerated to the extent of the wear layer. If the abrasion which is determined by the signal strength or the quality of the radio link between the antenna and the transponder is therefore present at this point on the hose wall to the extent of the wall thickness which is defined as the wear layer, the hose can continue to be operated. Otherwise, operation has to be interrupted.

According to a further aspect of the present invention, the transponder is preferably arranged spaced apart to a maximum extent in the radial direction from the hose interior within the wear layer. This has the advantage that in this system also the transponder can be removed, damaged or destroyed by the progressive abrasion out of the hose wall, so that its absence can be detected, and given knowledge of the position of the transponder, i.e. its radial position, it is possible to infer correspondingly deep abrasion at this point on the hose wall. An alarm can also be triggered in this case. It is particularly advantageous for this purpose if the transponder is arranged spaced apart to a maximum extent from the interior of the hose in the radial direction, because the radio link is then interrupted only when maximum permissible abrasion occurs.

According to a further aspect of the present invention, a multiplicity of transponders are embedded in the hose wall and are arranged offset with respect to one another in the circumferential direction and/or in the longitudinal direction. As a result of the offset in the longitudinal direction, the hose can be monitored for damage over its length. The offset in the circumferential direction ensures improved monitoring is possible over the flow cross section. This is particularly advantageous because, depending on the application and the position of the hose, areas on the inside of the hose wall which are loaded to differing degrees are formed, the position of which areas can only be predicted to a limited extent during operation. Therefore, by increasing the number of the transponders within a cross section, it is possible to draw reliable conclusions about the maximum abrasion occurring in this plane.

According to a further aspect of the present invention, at least three transponders are arranged offset with respect to one another, preferably by a maximum of 120°, in the circumferential direction essentially within the cross-sectional area. In this way, a cross-sectional area can be monitored comparatively well with manageable expenditure, and the maximum abrasion can be reliably detected with a high level of probability. This is the case, in particular, if the transponders are arranged offset with respect to one another by a maximum of 120°, in particular three transponders are arranged offset with respect to one another by approximately 120°.

According to a further aspect of the present invention, the antenna is arranged radially outside the wear layer, preferably within the minimum layer. As a result it is possible to promote a situation in which the antenna itself is not damaged by the abrasion. For this purpose, the antenna can be arranged outside the hose, i.e. separately, or on the outer surface thereof. The antenna is, however, preferably integrated into the minimum layer in order to protect it against external influences.

According to a further aspect of the present invention, the antenna is embodied and arranged in such a way that the electromagnetic coupling to the transponder can be composed essentially of the wear layer As a result, the energy which is necessary to operate the electromagnetic coupling, i.e. for the radio link, can be used as well as possible, i.e. the energy requirement for the radio link is minimised. In addition, only the areas of the hose material which are necessary to carry out the invention are penetrated electromagnetically. As a result, the surroundings are also kept very largely free of the electromagnetic radiation.

According to a further aspect of the present invention, the antenna is arranged offset in each case by 60° in the circumferential direction with respect to two transponders, essentially within a cross-sectional area. This ensures a minimum distance of the route of the radio link. In the case of three transponders, a uniform arrangement of the antenna with respect to the transponders is achieved at the same time.

According to a further aspect of the present invention, the antenna has an antenna line which is arranged linearly or wound in the longitudinal direction. A linear arrangement, i.e. straight along the longitudinal axis, minimizes the length of the antenna line and therefore the material used for it and costs as well as the energy requirement to operate the antenna. A wound or else undulating arrangement, i.e. with components of the profile of the antenna line arranged both in the longitudinal direction and transversely with respect thereto, i.e. obliquely, is advantageous because as a result the arrangement of the connections of the antenna line at the hose ends can be arranged more flexibly.

According to a further aspect of the present invention, the transponder can transmit an identifier, which identifies it unambiguously, to the antenna by means of the electromagnetic coupling. The transponder can be unambiguously identified by means of this identifier. If its position on the hose is known, that the signal strength or the quality of its radio link and by this means the abrasion at this point assigned its position in the hose.

An exemplary embodiment and further advantages of the invention are explained in the following text in conjunction with the following figures, in which: In the figures.

Figure 1:
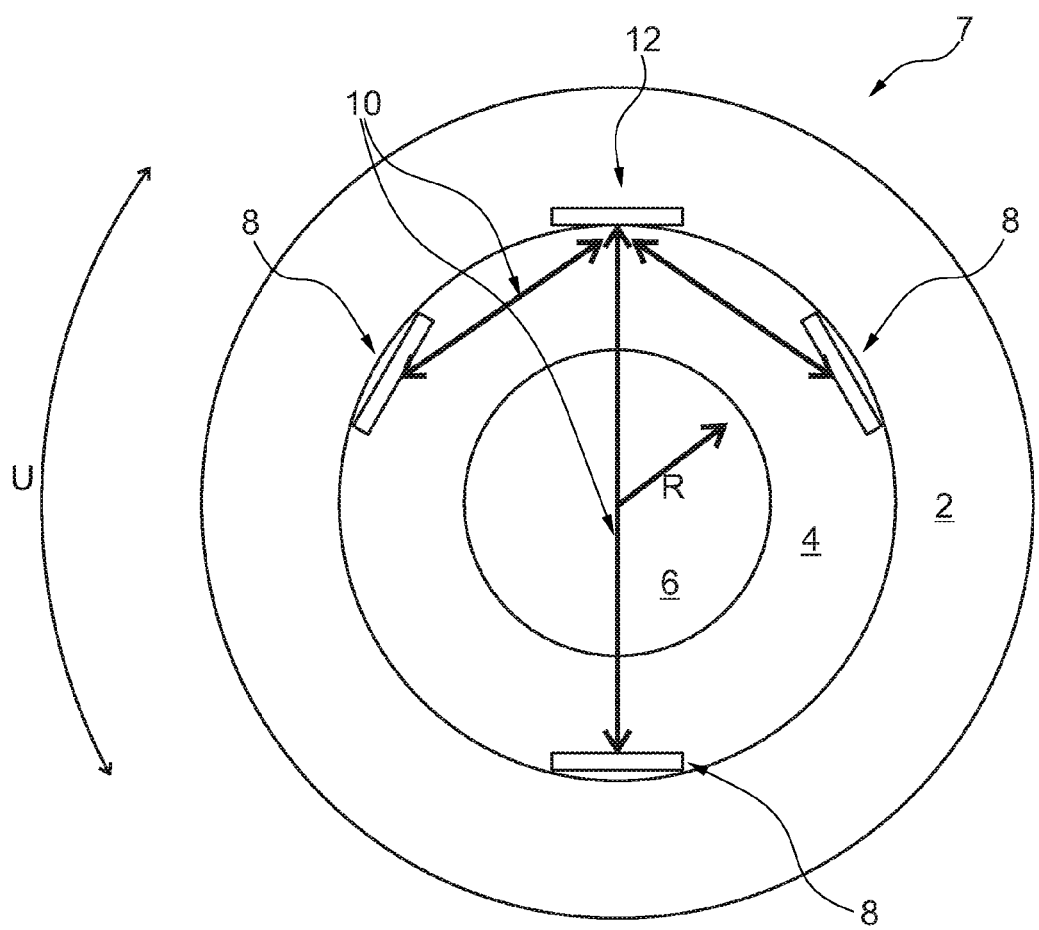
FIG. 1 shows a schematic illustration of a cross section through a hose according to the invention.

FIG. 1 shows a schematic illustration of a cross section through a hose 7 according to the invention. If a plurality of these hoses 7 are used in combination with one another, the individual hoses 7 can also be referred to as hose segments 7.

The hose 7 has, in the radial direction R, an outer minimum layer 2 and an inner wear layer 4, which together form the hose wall 2, 4. This hose wall 2, 4 encloses the hollow hose interior 6 which serves to convey a fluid medium. For example, the hose 7 can be used as a dredging hose 7 for conveying fluid-containing materials such as mud, sand, rock etc.

The hose 7 has three transponders 8 which are arranged offset with respect to one another by approximately 120° in a uniformly distributed fashion in the circumferential direction U in the illustrated cross-sectional area. The transponders 8 are each embedded in the hose wall 2, 4, specifically as close as possible to the minimum layer 2 within the wear layer 4.

The hose 7 also has an antenna 12 which runs in the longitudinal direction L of the hose 7 (cf. FIGS. 2 to 4), and in the illustrated cross-sectional area is arranged offset by approximately 60° in each case with respect to two of the transponders 8 in the circumferential direction U. The antenna 12 is arranged inside the minimum layer 2, and as close as possible to the wear layer 4 there.

By means of the antenna 12, in each case electromagnetic coupling 10 in the form of a radio link 10 to the transponders 8 can be set up from outside the hose 7. The antenna 12 is embodied and arranged in this case in such a way that the radio link 10 runs as far as possible through the wear layer 4 and the hose interior 6 through which the fluid medium to be conveyed flows during operation. In this context, each transponder 8 which is addressed by the antenna 12 transmits a unique identifier by means of which it can be identified. By means of knowledge of the arrangement of the transponders 8 in the course of the hose 7, the position of the currently addressed transponder 8 is then also known.

According to the invention, the determination of the dimension of the abrasion of the wear layer 4 is carried out by means of the signal strength or the quality of the radio link 10 i.e. by means of the transmitted identifier of the transponder 8 or by means of a separate signal, between the antenna 12 and the respective transponders 8 at this point or the area in between. This dimension can be determined e.g. by means of the RSSI value. In this context the RSSI value of the respective radio link 10, i.e. for each transponder 8, is defined at a specific time, e.g. in the case of a new and undamaged hose 7, or after inspection of the hose 7 from the inside by personnel, with the result that a known state of wear or of abrasion is known. In this state, the absolute or relative maximum RSSI value is available.

Owing to its (di)electric properties, both the material of the hose wall 2, 4 and the fluid medium to be conveyed influence the propagation of the electromagnetic fields of the radio link 10. If the wall thickness of the hose 7, i.e. the wear layer 4 is reduced by the abrasion by the fluid medium during operation of the hose 7, the cross-sectional area of the hose interior 7 which is filled with medium increases by the same amount. Since the wear layer 4 and the fluid medium in the hose interior 7 have different (di)electric properties, the propagation conditions for the electromagnetic field of the radio link 10 also change, and as a result the RSSI values of the transponders 8 also change. According to the invention, the degree of wear of the hose wall 2, 4 can be determined from these changes.

Figure 2:
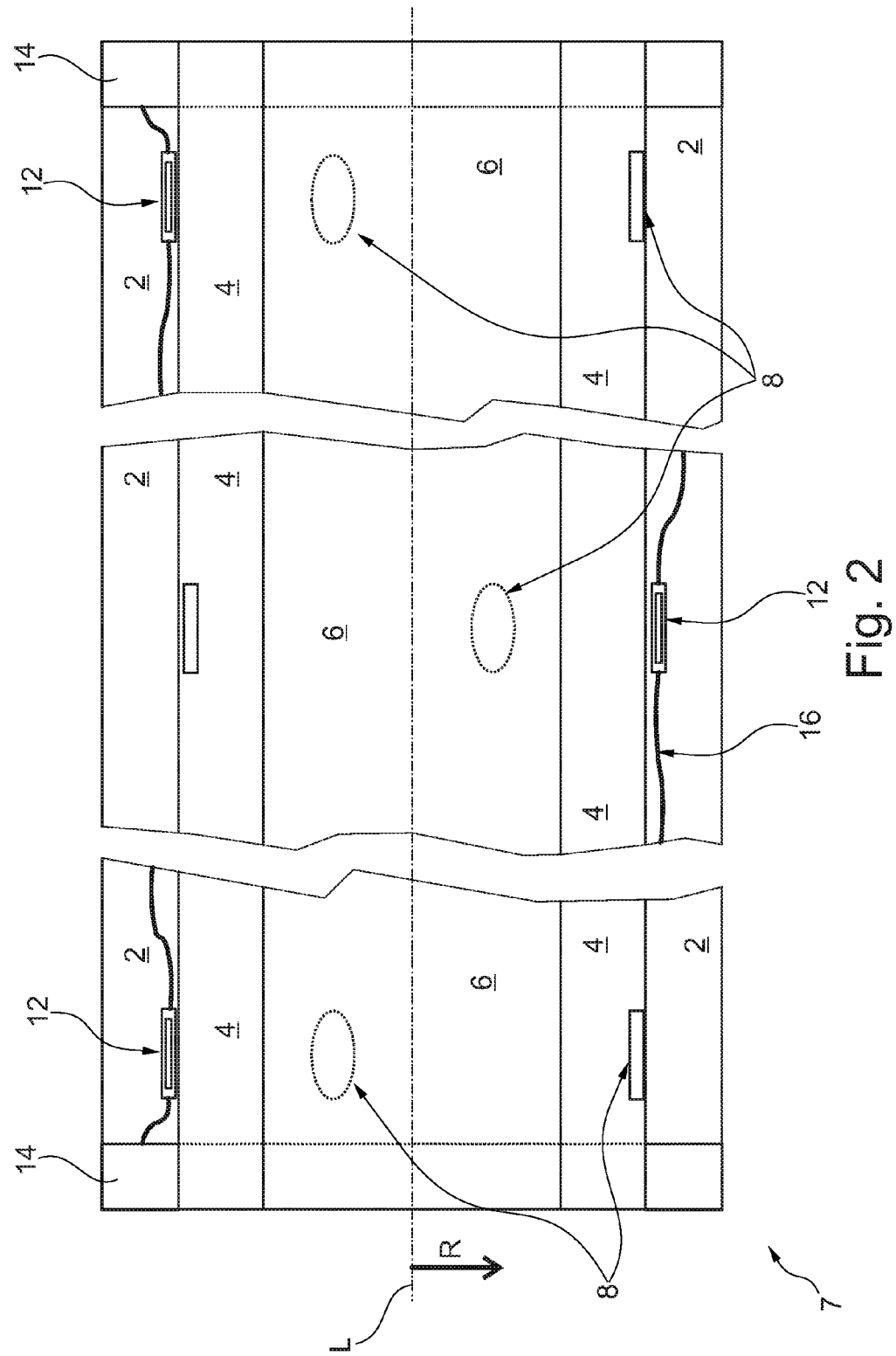
FIG. 2 shows a schematic illustration of a longitudinal section through a hose according to the invention.

FIG. 2 shows a schematic illustration of a longitudinal section through a hose 7 according to the invention. The arrangement of the three transponders 8 with the antenna 12 of the cross section in FIG. 1 is again represented in this illustration at three points, i.e. on the left, in the center and on the right, wherein these are each arranged rotated through approximately 60° with respect to one another. The antennas 12 are connected to one another in an electrically conductive fashion via an antenna line 16. The offset of the transponder antenna arrangements results in a wound profile of the antenna line 16 in the longitudinal direction L. The intermediate areas of the hose 7 are cut out in order to improve the illustration of the elements which are relevant to the invention. At the two ends, the hose 7 has in each case a hose segment coupling 14 so that it can be used as a segment of a relatively long hose and joined to other segments to form said hose.

Figure 3:
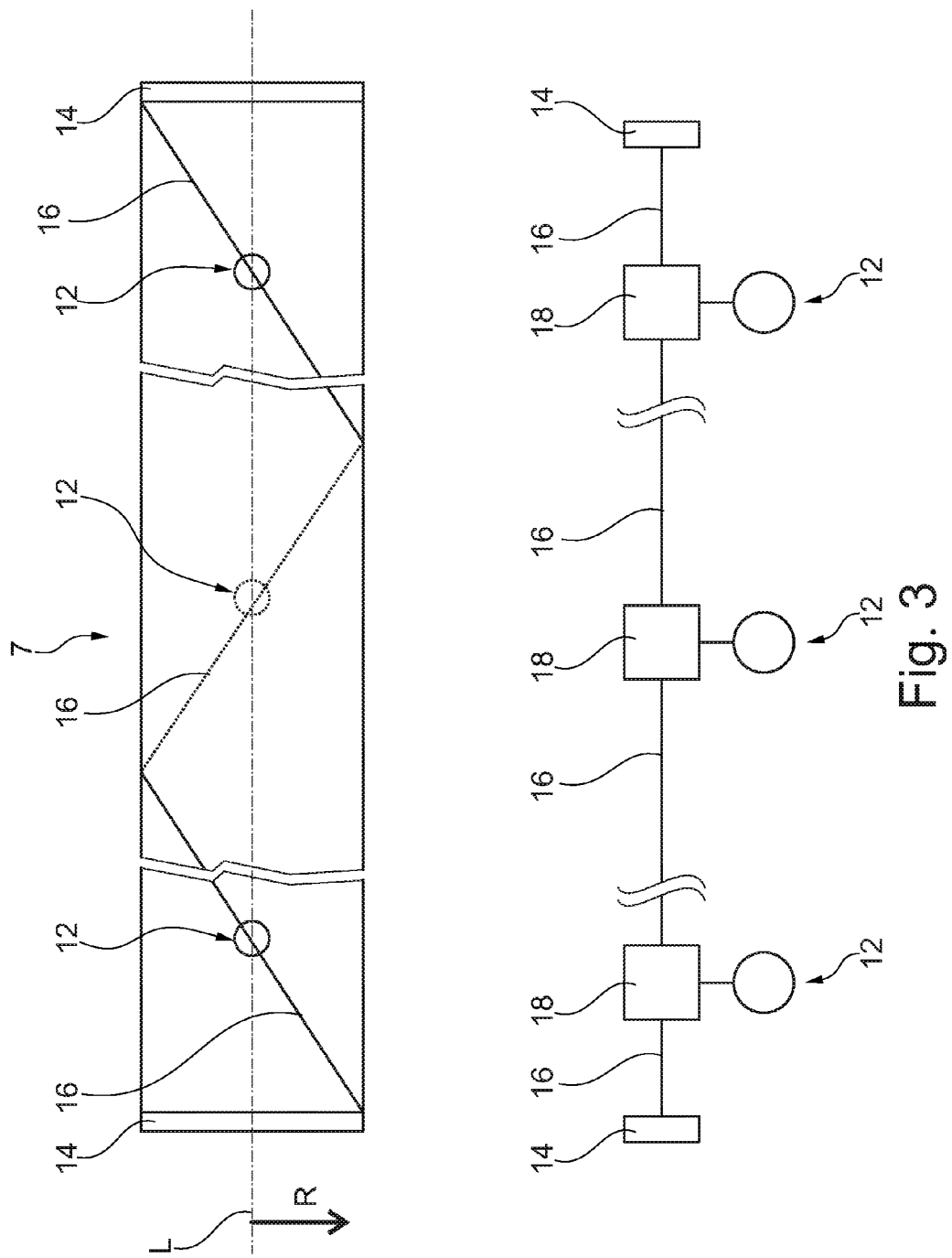
FIG. 3 shows a schematic illustration of a plan view, in the longitudinal direction, of a hose according to the invention (top) and a schematic electrical circuit diagram relating thereto (bottom)

FIG. 3 shows a schematic illustration of a plan view, in the longitudinal direction L, of a hose 7 according to the invention (top) and a schematic electrical circuit diagram relating thereto (bottom). The top illustration corresponds to the elements in FIG. 2. The bottom illustration of an electrical circuit diagram shows the two outer hose segment couplings 14 which each also have connections for connecting the respective antenna line 16 to the corresponding antenna line of the next segment or to an external evaluation device 24 (cf. FIG. 4). Within the hose 7, the antennas 12 are each connected via an adaptation network 8 to the common low-loss antenna line 16, which leads to both ends of the hose segment 7.

Figure 4:
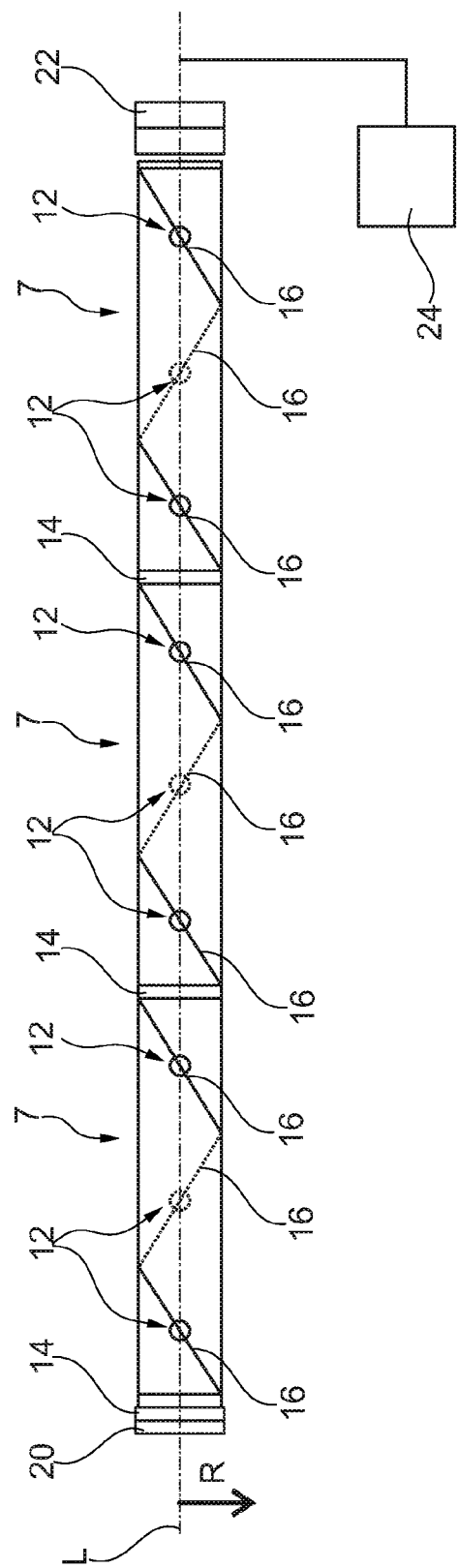
FIG. 4 shows a schematic illustration of a plan view, in the longitudinal direction, of a plurality of connected hoses according to the invention.

FIG. 4 shows a schematic illustration of a plan view in the longitudinal direction L of a plurality of connected hoses 7 according to the invention, i.e. of a hose with a plurality of hose segments 7. Here, the signals of the radio links 10 are input into the first hose segment 7 via the right-hand hose segment coupling 14 by means of a reading device 22, and transmitted to all the subsequent hose segments 7 via the hose segment couplings 14. The hose segment coupling 14 of the last hose segment 7 is provided with a termination impedance 20 which prevents the occurrence of reflections at the end of the line.

The reading device 22 at the start of the hose can address all the transponders 8 via the directed radio link, read out their data and pass it on to the evaluation device 24. In order to prevent transmission errors as a result of simultaneous responses by the transponders 8, the reading device 22 can switch the transponders 8 which have already been read out to a "mute" setting for a defined time period such as a reading-out cycle.

In addition to a unique identification number, each transponder 8 can additionally store information in its memory, such as e.g. the number of the segment 7 in which it is arranged. This information can be determined during the mounting of the hose 7 and transmitted to the transponder 8.

LIST OF REFERENCE SIGNS

Part of the Description

L Longitudinal direction
R Radial direction
U Circumferential direction
2 Outer minimum layer of the hose wall
4 Inner wear layer of the hose wall
6 Hose interior
7 Hose (segment)
8 Transponder (chip with antenna)
10 Electromagnetic coupling (HF/UHF)
12 (Measuring-) antenna
14 Hose segment coupling
16 Antenna line
18 Adaptation network
20 Termination impedance
22 Reading device (transmitter/receiver)
24 Evaluation device

The invention claimed is:

1. A hose comprising an integrated system for detecting damage, the hose comprising:
   a hose wall comprising at least one transponder is embedded therein;
   an antenna embedded in the hose wall;
   wherein the antenna and the transponder are electromagnetically coupled, and wherein strength of the electromagnetic coupling is a measure of the extent of damage to the hose wall.

2. The hose as claimed in claim 1, wherein the hose wall comprises an outer minimum layer and an inner wear layer, and wherein when the inner wear layer is eroded the thickness of the minimum layer is sufficient to ensure still reliable operation of the hose.

3. The hose as claimed in claim 2, wherein the transponder is arranged spaced apart to a maximum extent in the radial direction from the hose interior within the wear layer.

4. The hose as claimed in claim 1, wherein a plurality of transponders are embedded in the hose wall and are arranged offset with respect to one another in the circumferential direction (U) and/or in the longitudinal direction (L).

5. The hose as claimed in claim 4, wherein at least three transponders are arranged offset with respect to one another, by a maximum of 120° in the circumferential direction (U) within a cross-sectional area.

6. The hose as claimed in claim 2, wherein the antenna is arranged radially outside the inner wear layer and at least partially within the minimum layer.

7. The hose as claimed in claim 1, wherein the antenna is embodied and arranged in such a way that the electromagnetic coupling to the transponder can be composed essentially of the wear layer.

8. The hose as claimed in claim 4, wherein the antenna is arranged offset in each case by 60° in the circumferential direction (U) with respect to two transponders, essentially within a cross-sectional area.

9. The hose as claimed in claim 1, wherein the antenna has an antenna line which is arranged linearly or wound in the longitudinal direction (L).

10. The hose as claimed in claim 1, wherein the transponder can transmit an identifier, which identifies it unambiguously, to the antenna by the electromagnetic coupling.

11. The hose as claimed in claim 1, wherein quality of the electromagnetic coupling is also provided as a measure of the extent of damage to the hose wall.

12. A hose comprising an integrated system for detecting damage, the hose comprising:
    a hose wall comprising at least one transponder is embedded therein;
    an antenna embedded in the hose wall;
    wherein the antenna and the transponder are electromagnetically coupled, and wherein the strength and quality of the electromagnetic coupling is a measure of the extent of damage to the hose wall.

13. The hose as claimed in claim 12, wherein the hose wall comprises an outer minimum layer and an inner wear layer, and wherein when the inner wear layer is eroded the thickness of the minimum layer is sufficient to ensure still reliable operation of the hose.

14. The hose as claimed in claim 13, wherein the transponder is arranged spaced apart to a maximum extent in the radial direction from the hose interior within the wear layer.

15. The hose as claimed in claim 12, wherein a plurality of transponders are embedded in the hose wall and are arranged offset with respect to one another in the circumferential direction (U) and/or in the longitudinal direction (L).

16. The hose as claimed in claim 15, wherein at least three transponders are arranged offset with respect to one another, by a maximum of 120° in the circumferential direction (U) within a cross-sectional area.

17. A hose comprising an integrated system for detecting damage, the hose comprising:
    a hose wall comprising at least one transponder is embedded therein;
    an antenna embedded in the hose wall;
    wherein the antenna and the transponder are electromagnetically coupled, and wherein quality of the electromagnetic coupling is a measure of the extent of damage to the hose wall.

18. The hose as claimed in claim 17, wherein the hose wall comprises an outer minimum layer and an inner wear layer, and wherein when the inner wear layer is eroded the thickness of the minimum layer is sufficient to ensure still reliable operation of the hose.

19. The hose as claimed in claim 18, wherein the transponder is arranged spaced apart to a maximum extent in the radial direction from the hose interior within the wear layer.

20. The hose as claimed in claim 17, wherein a plurality of transponders are embedded in the hose wall and are arranged offset with respect to one another in the circumferential direction (U) and/or in the longitudinal direction (L).

* * * * *